United States Patent [19]

Kelly

[11] 4,215,214
[45] Jul. 29, 1980

[54] ENLARGED-HETERO-RING PROSTACYCLIN ANALOGS WITH 5-HALO FEATURE

[75] Inventor: Robert C. Kelly, Kalamazoo, Mich.

[73] Assignee: The Upjohn Company, Kalamazoo, Mich.

[21] Appl. No.: 935,300

[22] Filed: Aug. 21, 1978

Related U.S. Application Data

[60] Division of Ser. No. 819,941, Jul. 28, 1977, Pat. No. 4,124,599, which is a continuation-in-part of Ser. No. 725,547, Sep. 22, 1976, abandoned, which is a continuation-in-part of Ser. No. 716,771, Aug. 23, 1976, abandoned.

[51] Int. Cl.$^2$ ............................................. C07D 311/02
[52] U.S. Cl. ................................ 542/426; 260/345.2; 542/429
[58] Field of Search .................... 260/345.2; 542/426, 542/429

[56] References Cited

U.S. PATENT DOCUMENTS 4,150,222  4/1979  Johnson ............................... 542/426

*Primary Examiner*—Nicky Chan
*Attorney, Agent, or Firm*—Morris L. Nielsen; Robert A. Armitage

[57] ABSTRACT

Prostaglandin (PG$_1$) derivatives having (1) a 6-keto feature, together with a 9-deoxy-9-hydroxymethyl feature for example

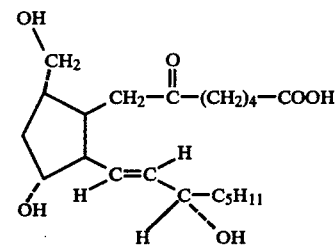

or (2) a 9-deoxy-6,9-epoxymethano feature together with a 5-halo or 6-hydroxy feature, for example

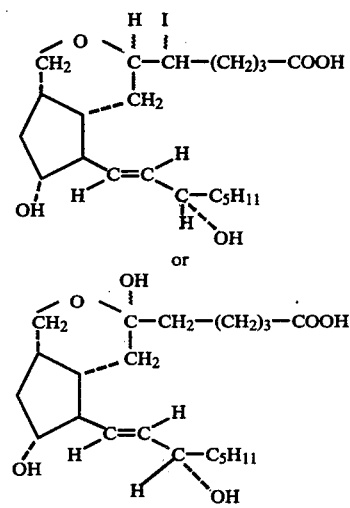

or a 5,6-didehydro feature, for example in an enol ether of the formula

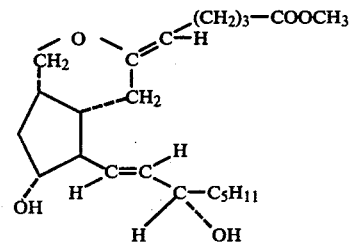

said derivatives having pharmacological activity. Processes for preparing them and the appropriate intermediates are disclosed.

25 Claims, No Drawings

ENLARGED-HETERO-RING PROSTACYCLIN ANALOGS WITH 5-HALO FEATURE

CROSS REFERENCE TO RELATED APPLICATIONS

This application is a division of then copending application Ser. No. 819,941 filed July 28, 1977, now issued as U.S. Pat. No. 4,124,599, which was a continuation-in-part of then copending application Ser. No. 725,547 filed Sept. 22, 1976, since abandoned, which was a continuation-in-part of then copending application Ser. No. 716,771 filed Aug. 23, 1976, since abandoned.

INCORPORATION BY REFERENCE

The essential material for this application, including the background of the invention, the disclosure of the invention, and the description of the preferred embodiments, including Preparations and Examples, is incorporated by reference from issued U.S. Pat. No. 4,124,599, under the provisions of M.P.E.P. 608.01(p).

BACKGROUND OF THE INVENTION

This invention relates to prostaglandin derivatives and to a process for preparing them.

The prostaglandins and analogs are well-known organic compounds derived from prostanoic acid which has the following structure and atom numbering:

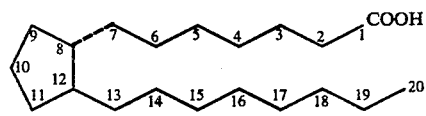

As drawn hereinafter the formulas represent a particular optically active isomer having the same absolute configuration as PGE$_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For background on prostaglandins, see for example Bergstrom et al., Pharmacol. Rev. 20, 1 (1968). For related compounds see Pace-Asciak et al., Biochem. 10, 3657 (1971). Related compounds are described in a publication on 6-keto-prostaglandin F$_{1\alpha}$ by Pace-Asciak, J. Am. Chem. Soc. 98, 2348 (1976) and a publication on "PGX" (6,9α-oxido-9α,15α-dihydroxyprosta-(Z)5, (E)13-dienoic acid) by E. J. Corey et al., J. Am. Chem. Soc. 99, 20006 (1977).

Some of the compounds of this invention may be regarded as analogs of prostacyclin and prostacyclin-type compounds.

Prostacyclin, an organic compound related to prostaglandins, is (5Z)-9-deoxy-6,9α-epoxy-Δ$^5$-PGF$_1$ and is represented by the formula

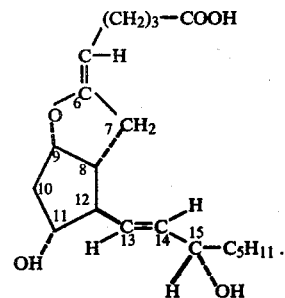

For its synthesis and structure see for example R. A. Johnson et al., J. Am. Chem. Soc. 99, 4182 (1977) and Prostaglandins 12, 915 (1976), and E. J. Corey et al., cited above. For some of its biological properties and uses see the references cited in the Johnson references. Prostacyclin is referred to as "PGI$_2$," see Anonymous, Prostaglandins 13, 375 (1977).

SUMMARY OF THE INVENTION

It is the purpose of this invention to provide novel products having pharmacological activity. It is a further purpose to provide processes for preparing these products and their intermediates.

Accordingly, there is provided a compound of the formula:

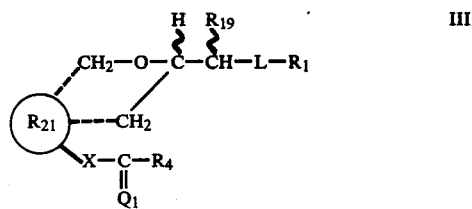

wherein L is
(1) —(CH$_2$)$_d$—C(R$_2$)$_2$—
(2) —CH$_2$—O—CH$_2$—Y— or
(3) —CH$_2$CH=CH—
wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—,
wherein Q is

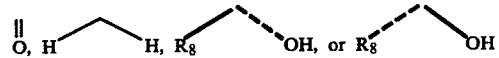

wherein R$_8$ is hydrogen or alkyl of one to 4 carbon atoms, inclusive,
wherein R$_1$ is
(1) —COOR$_3$
(2) —CH$_2$OH
(3) —CH$_2$N(R$_9$)(R$_{18}$)

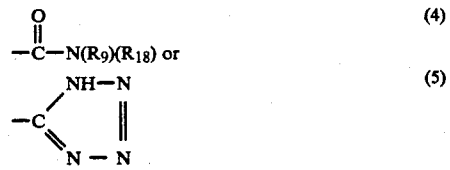

wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

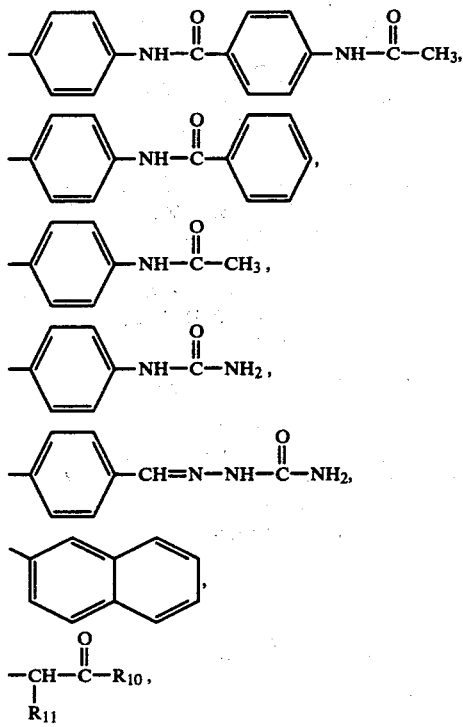

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_9$ is hydrogen, methyl, or ethyl, and $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;
wherein $R_4$ is

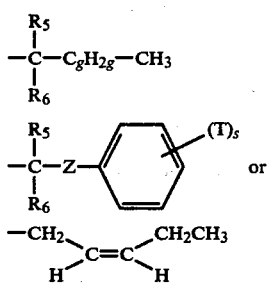

wherein $C_gH_{2g}$ is alkylene of one to 9 carbon atoms, inclusive, with one to 5 carbon atoms, inclusive, in the chain between $-CR_5R_6-$ and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6-$ and the phenyl ring; wherein T is alkyl of one to 4 carbon atoms, inclusive, fluoro, chloro, trifluoromethyl, or —$OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different; and
wherein X is
(1) trans—CH=CH—
(2) cis—CH=CH—
(3) —C≡C— or
(4) —CH$_2$CH$_2$—;
including the lower alkanoates thereof.

In compounds of formula III, $R_{19}$ is chloro, bromo, or iodo. In compounds of formula II and III, the wavy line ∼ indicates attachment in alpha or beta configuration. In compounds of formula III, $Q_1$ is

and $R_{21}$ is

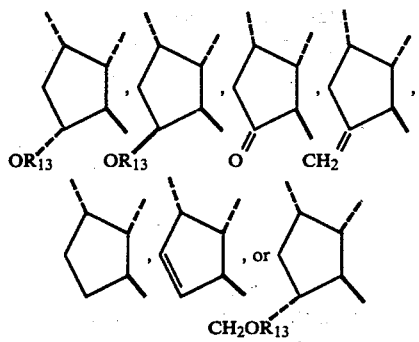

In formula III, $R_{13}$ is (a) hydrogen, (b) tetrahydropyranyl, (c) tetrahydrofuranyl, (d) 1-ethoxyethyl, (e) a group of the formula

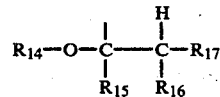

wherein $R_{14}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{15}$ and $R_{16}$ are the same or different, being hydrogen, alkyl of one to 4 carbon atoms, inclusive, phenyl or phenyl substituted with one, 2, or 3 alkyl of one to 4 carbon atoms, inclusive, or, when $R_{15}$ and $R_{16}$ are taken together —(CH$_2$)$_a$— or —(CH$_2$)$_b$—O—(CH$_2$)$_c$— wherein a is 3, 4, or 5, b is one, 2, or 3, and c is one, 2, or 3 with the proviso that b plus c is 2, 3, or 4, and wherein $R_{17}$ is hydrogen or phenyl, or (f) carboxyacyl including

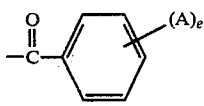

wherein "A" is alkyl of one to 4 carbon atoms, inclusive, bromo, phenylalkyl of 7 to 10 carbon atoms, inclusive, or nitro, and "e" is zero to 5, inclusive, provided that not more than two A's are other then alkyl, and that the total number of carbon atoms in the A's does not exceed 10 carbon atoms,

wherein $R_{30}$ is alkyl of one to 4 carbon atoms, inclusive,

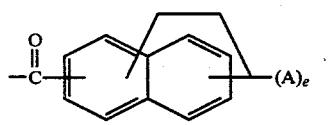

wherein "A" and "e" are as defined above, or

wherein $R_{31}$ is alkyl of one to 7 carbon atoms, inclusive.

In formula III, as used herein, attachment to $R_{20}$ and $R_{21}$ corresponds to bonds to the cyclopentane ring at the C-8, C-9, and C-12 positions following prostaglandin nomenclature, thus:

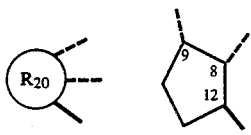

For those compounds of formula III wherein Q is

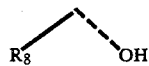

i.e. wherein the C-15 hydroxyl group is attached to the side chain in alpha configuration, the configuration at C-15 is identical with that of the naturally occuring prostaglandins such as $PGE_1$ obtained from mammalian tissues. The 15-epimer compounds are represented by formulas III when Q is

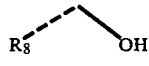

and are identified variously as "15-epi" or "15β" or "15R" by the appropriate prefix in the name. As is known in the art, "R" and "S" designations depend on the neighboring substituents. See. R. S. Cahn, J. Chem. Ed. 41, 116 (1964).

An example of the halo compounds of formula III is represented by the formula

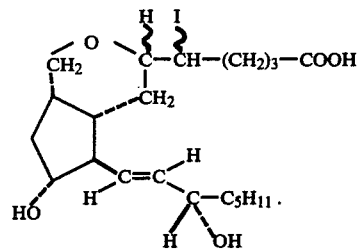

and named 5ξ-iodo-9-deoxy-6ξ,9α-epoxymethano-$PGF_1$.

I claim:

1. A compound of the formula

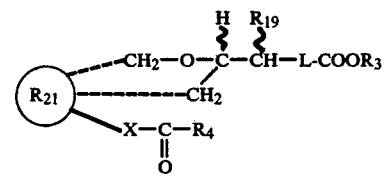

wherein $R_{21}$ is

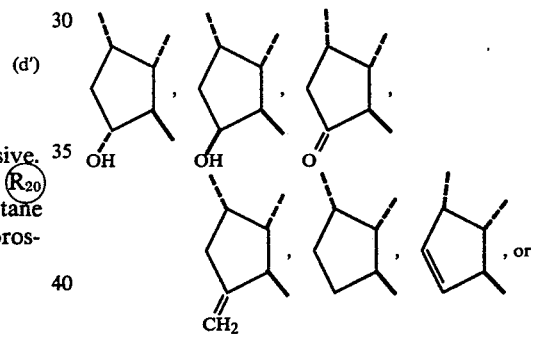

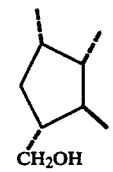

wherein L is
(1) —$(CH_2)_d$—$C(R_2)_2$—
(2) —$CH_2$—O—$CH_2$—Y— or
(3) —$CH_2CH=CH$—
wherein d is zero to 5, $R_2$ is hydrogen, methyl, or fluoro, being the same or different with the proviso that one $R_2$ is not methyl when the other is fluoro, and Y is a valence bond, —$CH_2$—, or —$(CH_2)_2$—,
wherein Q is $$\underset{O,}{\overset{\|}{C}} \quad \underset{H}{\overset{H}{\diagup\hspace{-0.5em}\diagdown}} \quad \underset{R_8}{\diagup\hspace{-0.5em}\diagdown}\underset{OH, or}{} \quad \underset{R_8}{\diagup\hspace{-0.5em}\diagdown}\underset{OH}{}$$

wherein $R_8$ is hydrogen or alkyl of one to 4 carbon atoms, inclusive,
wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

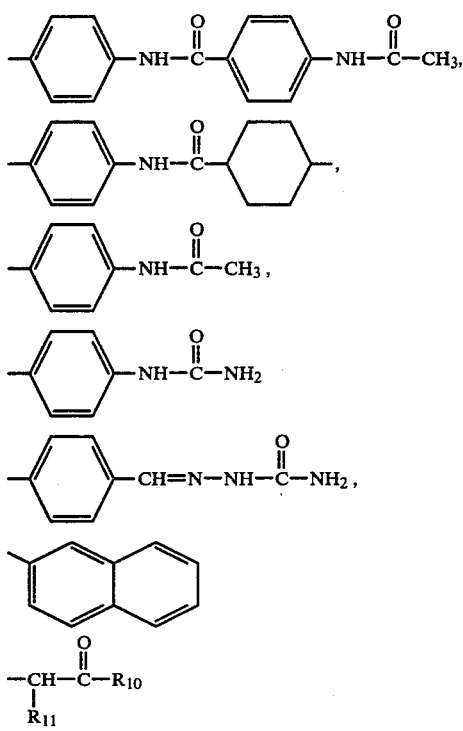

wherein R₁₀ is phenyl, p-bromophenyl, p-biphenylyl, p-nitrophenyl, p-benzamidophenyl, or 2-naphthyl, and wherein R₁₁ is hydrogen or benzoyl, or (n) a pharmacologically acceptable cation,
wherein R₄ is

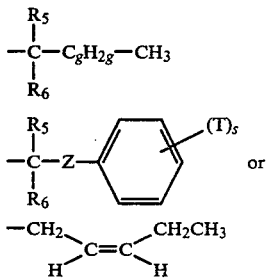

wherein $C_gH_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between CR₅R₆— and the phenyl ring;
wherein T is alkyl of one to 4 carbon atoms, inclusive, fluoro, chloro, trifluoromethyl, or —OR₇— wherein R₇ is alkyl of one to 4 carbon atoms, inclusive, and s is zero, one, 2, or 3, with the proviso that not more than two T's are other than alkyl and when s is 2 or 3 the T's are either the same or different;
wherein R₁₉ is chloro, bromo, or iodo; and wherein X is
(1) trans—CH=CH—
(2) cis—CH=CH—
(3) —C≡C— or
(4) —CH₂CH₂—
and wherein wavy line ∼ indicates attachment in alpha or beta configuration.

2. A compound according to claim 1 wherein (R₂₁) is

3. 5ξ-Iodo-9-deoxy-6ξ,9α-epoxymethano-11β-PGF₁, methyl ester, compounds according to claim 2.

4. A compound according to claim 1 wherein (R₂₁) is

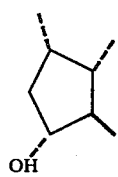

5. A compound according to claim 4 wherein L is —(CH₂)ₙ—, n being 3, 4, or 5, wherein Q is

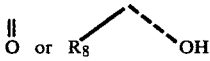

wherein R₈ is limited to hydrogen, methyl, or ethyl, and
wherein R₄ is n-pentyl, 1,1-dimethylpentyl, 1,1-difluoropentyl,

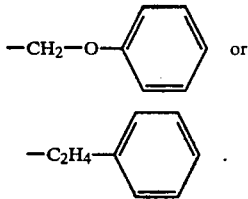

6. A compound according to claim 5 wherein X is —C≡C—.

7. 5-Bromo-9-deoxy-6ξ,9α-epoxymethano-15(S)-13,14-didehydro-PGF₁, methyl ester, compounds according to claim 6.

8. 5ξ-Bromo-9-deoxy-6ξ,9α-epoxymethano-15(R)-13,14-didehydro-PGF₁, methyl ester, compounds according to claim 6.

9. A compound according to claim 5 wherein X is trans-CH=CH—.

10. A compound according to claim 9 wherein R₃ is

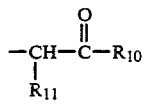

11. 5ξ-Iodo-9-deoxy-6ξ,9α-epoxymethano-PGF$_1$, p-phenylphenacyl ester, compounds according to claim 10.

12. A compound according to claim 9 wherein R$_3$ is hydrogen, alkyl of one to 12 carbon atoms, inclusive, or a pharmacologically acceptable cation.

13. A compound according to claim 12 wherein R$_3$ is hydrogen, methyl, or a pharmacologically acceptable cation.

14. 5ξ-Iodo-9-deoxy-6ξ,9α-epoxymethano-PGF$_1$, compounds according to claim 13.

15. 5ξ-Bromo-9-deoxy-6ξ,9α-epoxymethano-PGF$_1$, methyl ester, compounds according to claim 13.

16. 5ξ-Iodo-9-deoxy-6ξ,9α-epoxymethano-PGF$_1$, methyl ester compounds according to claim 13.

17. 5ξ-Iodo-9-deoxy-6ξ,9α-epoxymethano-15-keto-PGF$_1$, methyl ester, compounds according to claim 13.

18. 5ξ-Iodo-9-deoxy-6ξ,9α-epoxymethano-15-doexy-PGF$_2$, methyl ester, compounds according to claim 13.

19. 5ξ-Iodo-9-deoxy-6ξ,9α-epoxymethano-17-phenyl-18,19,20-trinor-PGF$_1$, methyl ester, compounds according to claim 13.

20. A compound according to claim 4, wherein L is —(CH$_2$)$_n$—, n being 3, 4, or 5, where Q is

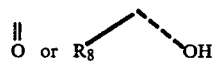

wherein R$_8$ is hydrogen, methyl or ethyl, and wherein R$_4$ is

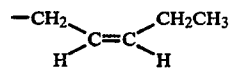

21. 5ξ-Iodo-9-deoxy-6ξ,9α-epoxymethano-17,18-didehydro-PGF$_1$, methyl ester, a compound according to claim 20.

22. (5R,6R)-5-Iodo-9-deoxy-6,9α-epoxymethano-PGF$_1$, methyl ester, a compound according to claim 16.

23. (5S,6S)-5-Iodo-9-deoxy-6,9α-epoxymethano-PGF$_1$, methyl ester, a compound according to claim 16.

24. (5R,6R)-5-Iodo-9-deoxy-6,9α-epoxymethano-17,18-didehydro-PGF$_1$, methyl ester, a compound according to claim 21.

25. (5S,6S)-5-Iodo-9-deoxy-6,9α-epoxymethano-17,18-didehydro-PGF$_1$, methyl ester, a compound according to claim 21.

* * * * *

UNITED STATES PATENT OFFICE
CERTIFICATE OF CORRECTION

Patent No. 4,215,214      Dated 29 July 1980

Inventor(s) Robert C. Kelly

It is certified that error appears in the above-identified patent and that said Letters Patent are hereby corrected as shown below:

Column 4, line 16, "(3) -C=C-" should read -- (3) -C≡C- --;

Column 6, that portion of the formula reading $$\underset{\underset{O}{\|}}{X-C-R_4} \text{ bonded to } (R_{21})$$

should read $$\underset{\underset{Q}{\|}}{X-C-R_4} \text{ bonded to } (R_{21})$$

Column 9, line 27 and 30, "5ξ-Iodo-" should read -- 5ξ-Iodo- --; line 30, "15-doexy-" should read -- 15-deoxy- --;

Column 10, line 1, "5ξ-Iodo-" should read -- 5ξ-Iodo- --.

Signed and Sealed this

*Twentieth* Day of *January 1981*

[SEAL]

*Attest:*

RENE D. TEGTMEYER

*Attesting Officer*     *Acting Commissioner of Patents and Trademarks*